US009132173B2

(12) United States Patent
Caboche et al.

(10) Patent No.: US 9,132,173 B2
(45) Date of Patent: Sep. 15, 2015

(54) EXPRESSION VECTOR FOR CHOLESTEROL 24-HYDROLASE IN THERAPY OF HUNTINGTON'S DISEASE

(75) Inventors: Jocelyne Caboche, Paris (FR); Patrick Aubourg, Paris (FR); Nathalie Cartier, Paris (FR); Sandrine Betuing, Paris (FR)

(73) Assignees: Institut National de la Sante et de la Recherche Medicale (INSERM), Paris (FR); Universite Paris Descartes, Paris (FR); Universite Evry Val d'essone, Evry (FR); Centre National de la Recherche Scientifique (CNRS), Paris (FR)

( * ) Notice: Subject to any disclaimer, the term of this patent is extended or adjusted under 35 U.S.C. 154(b) by 260 days.

(21) Appl. No.: 13/878,845

(22) PCT Filed: Oct. 14, 2011

(86) PCT No.: PCT/EP2011/068033
§ 371 (c)(1),
(2), (4) Date: Apr. 11, 2013

(87) PCT Pub. No.: WO2012/049314
PCT Pub. Date: Apr. 19, 2012

(65) Prior Publication Data
US 2013/0209410 A1    Aug. 15, 2013

(30) Foreign Application Priority Data
Oct. 15, 2010 (EP) .................................... 10306128

(51) Int. Cl.
*A61K 48/00* (2006.01)
*A61K 38/44* (2006.01)
*C12N 9/14* (2006.01)
*C12N 15/86* (2006.01)
*C12N 15/864* (2006.01)

(52) U.S. Cl.
CPC .................. *A61K 38/44* (2013.01); *A61K 48/00* (2013.01); *C12N 9/14* (2013.01); *C12N 15/86* (2013.01); *C12N 15/8645* (2013.01); *C12N 2750/14143* (2013.01); *C12N 2840/203* (2013.01)

(58) Field of Classification Search
None
See application file for complete search history.

(56) References Cited

U.S. PATENT DOCUMENTS 8,198,257 B2 *   6/2012   Aubourg et al. ............. 514/44 R

FOREIGN PATENT DOCUMENTS

WO      2004/055201 A2      7/2004
WO      WO 2009/034127   *  3/2009

OTHER PUBLICATIONS

Anonymous, "Liste de postes vacants. session 2011. Profil due poste 1666", Universite Paris 6 (Pierre et Marie Curie), Feb. 24, 2011, Web.
Hudry et al., "Adeno-associated Virus Gene Therapy With Cholesterol 24-Hydroxylase Reduces the Amyloid Pathology Before or after the Onset of Amyloid Plaques in Mouse Models of Alzheimer's Disease", Molecular Therapy, Aug. 4, 2009, pp. 44-53, vol. 18, No. 1.
Hudry et al., "AAV Gene Therapy with Cholesterol 24-Hydroxylase Reverses Alzheimer Phenotype of APP23 Mouse Model", Molecular Therapy, May 2009, p. 2148, vol. 17 supplement.
Van Raamsdonk et al., "Wild-type huntingtin ameliorates striatal neuronal atrophy but does not prevent other abnormalities in the YAC128 mouse model of Huntington disease", BMC Neuroscience, Dec. 5, 2006, p. 80, vol. 7, No. 1, Biomed Central, London, GB.
Trushina et al., "Tricyclic pyrone compounds prevent aggregation and reverse cellular phenotypes caused by expression of mutant huntingtin protein in striatal neurons", BMC Neuroscience, Jul. 8, 2009, p. 73, vol. 10, No. 1, Biomed Central, London, GB.
Van Ramsdonk et al., "Ethyl-EPA treatment improves motor dysfunction, but not neurodegeneration in the YAC128 mouse model of Huntington's disease", Experimental Neurology, Dec. 1, 2005, pp. 266-272, vol. 196, No. 2, Academic Press, NY.
Valenza et al., "Progressive dysfunction of the cholesterol biosynthesis pathway in the R6/2 mouse model of Huntington's disease", Neurobiology of Disease, Sep. 21, 2007, pp. 133-142, vol. 28, No. 1.
Trushina et al., "Mutant huntingtin inhibits clathrin-independent endocytosis and causes accumulation of cholesterol in vitro and in vivo", Human Molecular Genetics, Dec. 15, 2006, pp. 3578-3591, vol. 15, No. 24.
Sipione et al., "Early transcriptional profiles in huntingtin-inducible striatal cells by microarray analyses", Hum. Mol. Genet., 2002, pp. 1953-1965, vol. 11.
Valenza et al., "cholesterol defect is marked across multiple rodent models of Huntington's Disease and is manifest in astrocytes", Journal of Neuroscience, Aug. 11, 2010, pp. 10844-10850, vol. 30, No. 32.
Valenza et al., "Dysfunction of the cholesterol biosynthetic pathway in Huntington's disease", J Neurosci., Oct. 26, 2005, vol. 25, No. 43.
Valenza, "Cholesterol dysfunction in neurodegenerative diseases: is Huntington's disease on the list?", Prog Neurobiol., Jun. 20, 2001, pp. 165-176, vol. 80, No. 4.
Block et al, "Altered cholesterol and fatty acid metabolism in Huntington disease", J Clin Lipidol., Jan. 2010, pp. 17-23, vol. 4, No. 1.

(Continued)

*Primary Examiner* — Michael Burkhart
(74) *Attorney, Agent, or Firm* — Whitham, Curtis, Christofferson & Cook, P.C.

(57) ABSTRACT

The present invention relates to a vector for use in the treatment of Huntington's disease, which vector comprises a cholesterol 24-hydroxylase encoding nucleic acid.

13 Claims, 10 Drawing Sheets

(56) References Cited

OTHER PUBLICATIONS

Figure 1:
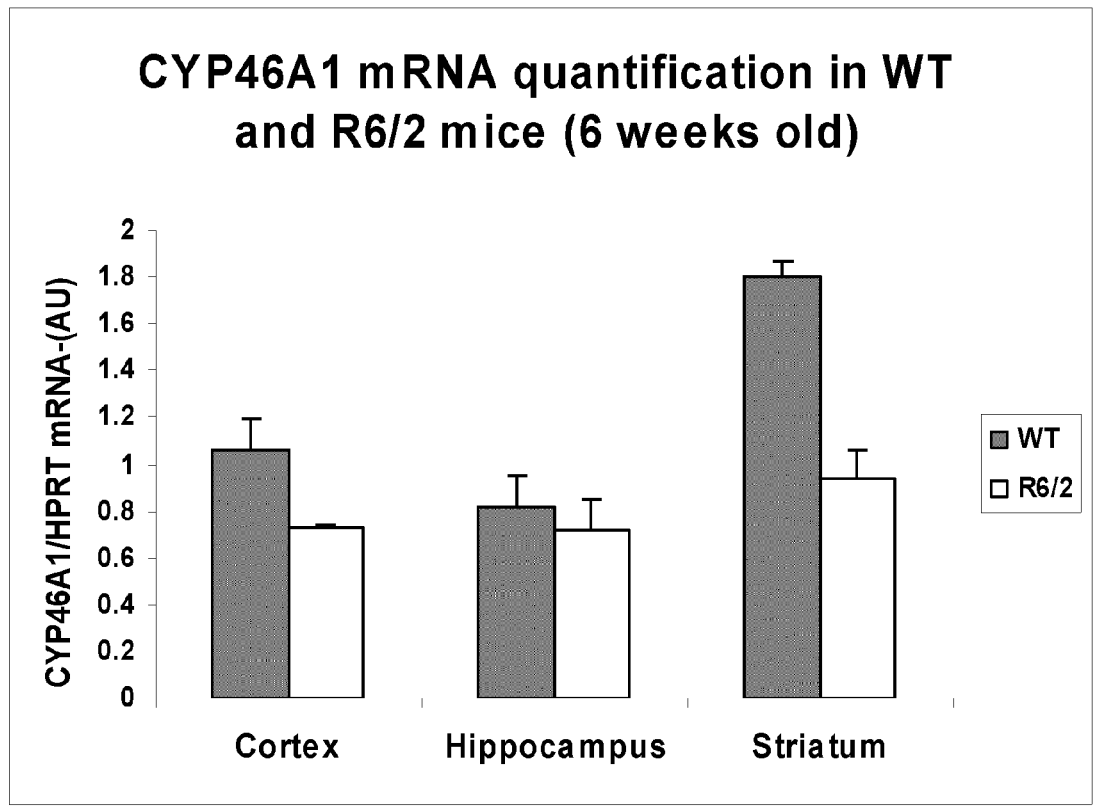

Liu et al., "Cholesterol involvement in the pathogenesis of neurodegenerative diseases", Mol Cell Neurosci., Aug. 4, 2009, vol. 43, No. 1.

Brochier et al., "Quantitative gene expression profiling of mouse brain regions reveals differential transcripts conserved in human and affected in disease model", Physiol Genomics., Feb. 5, 2008, pp. 170-179, vol. 33, No. 2.

Roze et al., "Mitogen- and stress-activated protein kinase-1 deficiency is involved in expanded-huntingtin-induced transcriptional dysregulation and striatal death", FASEB J., Aug. 20, 2001, pp. 1083-1093, vol. 22, No. 4.

Becanovic et al., "Transcriptional changes in Huntington disease identified using genome-wide expression profiling and cross-platform analysis", Hum Mol Genet., Jan. 20, 2010, pp. 1438-1452, vol. 19, No. 8.

Russell et al., "Cholesterol 24-Hydroxylase: An Enzyme of Cholesterol Turnover in the Brain", Annual Review of Biochemistry, Jun. 1, 2009, pp. 1017-1040, vol. 78, No. 1.

Leoni et al., "Cholesterol biosynthesis is impaired in Huntington's disease patients: implication for brain cholesterol homeostasis", European Journal of Neurology, Oct. 2009, p. 166, vol. 16, No. suppl 3.

Halford et al, "Reduction of cholesterol synthesis in the mouse brain does not affect amyloid formation in Alzheimer's disease, but does extend lifespan", Proceedings of the National Academy of Sciences, Mar. 3, 2009, pp. 3502-3506, vol. 106, No. 9.

Kotti et al., "Brain cholesterol turnover required for geranylgeraniol production and learning in mice", Proceedings of the National Academy of Sciences, Mar. 7, 2006, pp. 3869-3874, vol. 103, No. 10.

Milagre et al., "Transcriptional regulation of the human CYP46A1 brain-specific expression by Sp transcriptional factors", Journal of Neurochemistry, Jul. 1, 2008, pp. 835-849, vol. 106, No. 2.

Martin et al., "Mitogen- and stress-activated protein kinase 1-induced neuroprotection in Huntington's disease: role on chromatin remodeling at the PGC-1-alpha promoter", Hum Mol Genet., Apr. 14, 2011, pp. 2422,2434, vol. 20, No. 12.

* cited by examiner

EXPRESSION VECTOR FOR CHOLESTEROL 24-HYDROLASE IN THERAPY OF HUNTINGTON'S DISEASE

CROSS-REFERENCE TO RELATED APPLICATIONS

This application is a Rule 371 national stage filing from International patent application PCT/EP2011/068033 filed 14 Oct. 2011.

FIELD OF THE INVENTION

The present invention relates to a vector for use in the treatment of Huntington's disease, which vector comprises a cholesterol 24-hydroxylase encoding nucleic acid.

BACKGROUND OF THE INVENTION

Huntington disease (HD) is the most frequent neurodegenerative disease caused by an expansion of glutamines repeats. The main clinical manifestations of HD are chorea, cognitive impairment and psychiatric disorders. The transmission of HD is autosomic dominant with a complete penetrance. The mutation responsible for HD, an unstable expansion of CAG repeat sequence, is located at the 5' terminal part of the IT15 gene encoding the Huntingtin (htt). One important characteristic of HD is the vulnerability of a particular brain region, the striatum, despite similar expression of the mutated protein in other brain areas (Roze et al., 2008a). Furthermore, despite the early expression of mutated Htt (Exp-Htt) in all neuronal cells, ie as soon as birth, the first symptoms and neuropathological hallmarks appear at adulthood, around 40-45 years old. The age of onset of the disease is conversely proportional to the number of CAG repeats in the affected allele. Once the first symptoms have appeared, the disease progresses and leads progressively to death. One currently admitted hypothesis is that alteration of specific signalling pathways during ageing increases Exp-Htt-induced molecular alterations, specifically or primarily in striatal neurons. So far, there are no available therapies aimed at slowing down disease progression and consequently HD progresses inexorably to death. Thus, it is important to find strategies for therapy in HD.

SUMMARY OF THE INVENTION

The inventors observed that CYP46A1, an enzyme responsible of the degradation of cholesterol in the central nervous system, is neuroprotective in a cellular model of HD. Moreover, the inventors observed a reduction of CYP46A1 mRNAs in the striatum, the more vulnerable brain structure in the disease, of the R6/2 transgenic HD mouse model.

Thus, the invention relates to a vector for the treatment of Huntington's disease, wherein the vector expresses CYP46A1 in cells of the central nervous system.

Moreover, the invention relates to a pharmaceutical composition for use in the treatment of Huntington's disease which comprises a vector according to the invention.

DETAILED DESCRIPTION OF THE INVENTION

Definitions

Throughout the specification, several terms are employed and are defined in the following paragraphs.

The CYP46A1 Sequences

A first object of the invention relates to a vector for use in the treatment of Huntington's disease, which vector comprises the full sequence of cholesterol 24-hydroxylase encoding nucleic acid.

As used herein, the term "gene" refers to a polynucleotide containing at least one open reading frame that is capable of encoding a particular polypeptide or protein after being transcribed or translated.

As used herein, the terms "coding sequence" or "a sequence which encodes a particular protein", denotes a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

The CYP46A1 gene encodes cholesterol 24-hydroxylase. This enzyme is a member of the cytochrome P450 superfamily. A cDNA sequence for CYP46A1 is disclosed in Genbank Access Number AF094480.1 (SEQ ID NO:1). The amino acid sequence is shown in SEQ ID NO:2.

In a preferred embodiment, the invention provides a nucleic acid construct comprising sequence SEQ ID No 1 or a variant thereof for the treatment of Huntington's disease.

The variants include, for instance, naturally-occurring variants due to allelic variations between individuals (e.g., polymorphisms), alternative splicing forms, etc. The term variant also includes CYP46A1 gene sequences from other sources or organisms. Variants are preferably substantially homologous to SEQ ID No 1, i.e., exhibit a nucleotide sequence identity of typically at least about 75%, preferably at least about 85%, more preferably at least about 90%, more preferably at least about 95% with SEQ ID No 1. Variants of a CYP46A1 gene also include nucleic acid sequences, which hybridize to a sequence as defined above (or a complementary strand thereof) under stringent hybridization conditions. Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

Non Viral Vectors

In a preferred embodiment, the vector use according to the invention is a non viral vector. Typically, the non viral vector may be a plasmid encoding CYP46A1.

The Viral Vectors

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The terms "Gene transfer" or "gene delivery" refer to methods or systems for reliably inserting foreign DNA into host cells. Such methods can result in transient expression of non integrated transferred DNA, extrachromosomal replication and expression of transferred replicons (e.g., episomes), or integration of transferred genetic material into the genomic DNA of host cells.

Examples of viral vector include adenoviral, retroviral, lentiviral, herpesvirus and adeno-associated virus (AAV) vectors.

Such recombinant viruses may be produced by techniques known in the art, such as by transfecting packaging cells or by transient transfection with helper plasmids or viruses. Typical examples of virus packaging cells include PA317 cells, Psi-CRIP cells, GPenv+ cells, 293 cells, etc. Detailed protocols for producing such replication-defective recombinant viruses may be found for instance in WO95/14785, WO96/22378, U.S. Pat. No. 5,882,877, U.S. Pat. No. 6,013,516, U.S. Pat. No. 4,861,719, U.S. Pat. No. 5,278,056 and WO94/19478.

In a preferred embodiment, adeno-associated viral (AAV) vectors are employed.

In another preferred embodiment, the AAV vector is AAV1, AAV2, AAV3, AAV4, AA5, AAV6, AAV7, AAV8, AAV9 AAV10 or any other serotypes of AAV that can infect human, monkeys or other species.

In a more preferred embodiment, the AAV vector is an AAV10.

By an "AAV vector" is meant a vector derived from an adeno-associated virus serotype, including without limitation, AAV-1, AAV-2, AAV-3, AAV-4, AAV-5, AAV6, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g, by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the DNA of interest (i.e. the CYP46A1 gene) and a transcriptional termination region.

The control elements are selected to be functional in a mammalian cell. The resulting construct which contains the operatively linked components is bounded (5' and Y) with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds.) for the AAV-2 sequence. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV6, etc. Furthermore, 5' and 3'ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Additionally, AAV ITRs may be derived from any of several AAV serotypes, including without limitation, AAV-1, AAV-2, AAV-3, AAV-4, AAV 5, AAV6, etc. Furthermore, 5' and 3'ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

Particularly preferred are vectors derived from AAV serotypes having tropism for and high transduction efficiencies in cells of the mammalian CNS, particularly neurons. A review and comparison of transduction efficiencies of different serotypes is provided in Cearley C N et al., 2008. In one preferred example, AAV2 based vectors have been shown to direct long-term expression of transgenes in CNS, preferably transducing neurons. In other nonlimiting examples, preferred vectors include vectors derived from AAV10 and AAV11 serotypes, which have also been shown to transduce cells of the CNS (Davidson et al, supra).

The selected nucleotide sequence is operably linked to control elements that direct the transcription or expression thereof in the subject in vivo. Such control elements can comprise control sequences normally associated with the selected gene.

Alternatively, heterologous control sequences can be employed. Useful heterologous control sequences generally include those derived from sequences encoding mammalian or viral genes. Examples include, but are not limited to, the phosphoglycerate kinase (PKG) promoter, CAG, neuronal promoters, promoter of Dopamine-1 receptor and Dopamine-2 receptor, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.). For purposes of the present invention, both heterologous promoters and other control elements, such as CNS-specific and inducible promoters, enhancers and the like, will be of particular use.

Examples of heterologous promoters include the CMV promoter. Examples of CNS specific promoters include those isolated from the genes from myelin basic protein (MBP), glial fibrillary acid protein (GFAP), and neuron specific enolase (NSE).

Examples of inducible promoters include DNA responsive elements for ecdysone, tetracycline, hypoxia andaufin.

The AAV expression vector which harbors the DNA molecule of interest bounded by AAV ITRs, can be constructed by directly inserting the selected sequence (s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994. Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge, 1981; Nambair et al., 1984; Jay et al., 1984. In order to producer AAV virions, an AAV expression vector is introduced into a suitable host cell using known techniques, such as by transfection. A number of transfection techniques are generally known in the art. See, e.g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Felgner et al., 1987), and nucleic acid delivery using high-velocity microprojectiles (Klein et al., 1987).

For instance, a preferred viral vector, such as the AAV10, comprises, in addition to a cholesterol 24-hydroxylase encoding nucleic acid sequence, the backbone of AAV vector with ITR derived from AAV-2, the promoter, such as the mouse PGK (phosphoglycerate kinase) gene or the cytomegalovirus/β-actin hybrid promoter (CAG) consisting of the enhancer from the cytomegalovirus immediate gene, the promoter, splice donor and intron from the chicken β-actin gene, the splice acceptor from rabbit β-globin, or any neuronal promoter such as the promoter of Dopamine-1 receptor or Dopamine-2 receptor with or without the wild-type or mutant form of woodchuck hepatitis virus post-transcriptional regulatory element (WWPRE).

Delivery of the Vectors

It is herein provided a method for treating Huntington's disease in a subject, said method comprising:

(a) providing a vector as defined above, which comprises a cholesterol 24-hydroxylase encoding nucleic acid; and (b) delivering the vector to the central nervous system (CNS) of the subject, whereby said vector transduces cells in the CNS, and whereby cholesterol 24-hydroxylase is expressed by the transduced cells at a therapeutically effective level.

Methods of delivery of vectors to neurons and/or astrocytes includes generally any method suitable for delivery vectors to the neurons and/or astrocytes such that at least a portion of cells of a selected synaptically connected cell population is transduced. The vector may be delivered to any cells of the central nervous system, or both. Generally, the vector is delivered to the cells of the central nervous system, including for example cells of the spinal cord, brainstem (medulla, pons, and midbrain), cerebellum, diencephalon (thalamus, hypothalamus), telencephalon (corpus striatum, cerebral cortex, or, within the cortex, the occipital, temporal, parietal or frontal lobes), or combinations thereof, or preferably any suitable subpopulation thereof. Further preferred sites for delivery include the ruber nucleus, corpus amygdaloideum, entorhinal cortex and neurons in ventralis lateralis, or to the anterior nuclei of the thalamus.

To deliver the vector specifically to a particular region and to a particular population of cells of the CNS, the vector may be administered by stereotaxic microinjection. For example, patients have the stereotactic frame base fixed in place (screwed into the skull). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of AAV vector injection) and trajectory. The software directly translates the trajectory into 3 dimensional coordinates appropriate for the stereotactic frame. Burr holes are drilled above the entry site and the stereotactic apparatus positioned with the needle implanted at the given depth. The AAV vector is then injected at the target sites. Since the AAV vector integrates into the target cells, rather than producing viral particles, the subsequent spread of the vector is minor, and mainly a function of passive diffusion from the site of injection and of course the desired transsynaptic transport, prior to integration. The degree of diffusion may be controlled by adjusting the ratio of vector to fluid carrier.

Additional routes of administration may also comprise local application of the vector under direct visualization, e.g., superficial cortical application, or other nonstereotactic application. The vector may be delivered intrathecally, in the ventricules or by intravenous injection.

The target cells of the vectors of the present invention are cells of the central nervous systems of a subject afflicted with Huntington's disease. Preferably the subject is a human being, generally an adult.

However the invention encompasses delivering the vector to biological models of the disease. In that case, the biological model may be any mammal at any stage of development at the time of delivery, e.g., embryonic, fetal, infantile, juvenile or adult, preferably it is an adult. Furthermore, the target CNS cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e.g. zebrafish model system).

Preferably, the method of the invention comprises intracerebral administration through stereotaxic injections. However, other known delivery methods may also be adapted in accordance with the invention. For example, for a more widespread distribution of the vector across the CNS, it may be injected into the cerebrospinal fluid, e.g., by lumbar puncture. To direct the vector to the peripheral nervous system, it may be injected into the spinal cord or into the peripheral ganglia, or the flesh (subcutaneously or intramuscularly) of the body part of interest. In certain situations the vector can be administered via an intravascular approach. For example, the vector can be administered intra-arterially (carotid) in situations where the blood-brain barrier is disturbed or not disturbed. Moreover, for more global delivery, the vector can be administered during the "opening" of the blood-brain barrier achieved by infusion of hypertonic solutions including mannitol.

The vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes.

The preferred doses and regimen may be determined by a physician, and depend on the age, sex, weight, of the subject, and the stage of the disease. As an example, for delivery of cholesterol 24-hydroxylase using a viral expression vector, each unit dosage of cholesterol 24-hydroxylase expressing vector may comprise 2.5 to 100 µl of a composition including a viral expression vector in a pharmaceutically acceptable fluid at a concentration ranging from $10^{11}$ to $10^{16}$ viral genome per ml for example.

Pharmaceutical Composition

A second object of the invention concerns a pharmaceutical composition for use in the treatment of Huntington's disease which comprises a therapeutically effective amount of a vector according to the invention.

By a "therapeutically effective amount" is meant a sufficient amount of the vector of the invention to treat Huntington's disease at a reasonable benefit/risk ratio applicable to any medical treatment.

It will be understood that the total daily dosage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range per adult per day. The therapeutically effective amount of the vector according to the invention that should be administered, as well as the dosage for the treatment of a pathological condition with the number of viral or non-viral particles and/or pharmaceutical compositions of the invention, will depend on numerous factors, including the age and condition of the patient, the severity of the disturbance or disorder, the method and frequency of administration and the particular peptide to be used.

The presentation of the pharmaceutical compositions that contain the vector according to the invention may be in any form that is suitable for intracerebral, intrathecal, intraventricular or intravenous administration.

In the pharmaceutical compositions of the present invention for intramuscular, intravenous, intracerebral, intrathecal or intraventricular administration, the active principle, alone or in combination with another active principle, can be administered in a unit administration form, as a mixture with conventional pharmaceutical supports, to animals and human beings.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The vector according to the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

Multiple doses can also be administered.

The invention will be further illustrated by the following figures and examples. However, these examples and figures should not be interpreted in any way as limiting the scope of the present invention.

FIGURES

FIG. 1: Quantification of CYP46A1 mRNA expression in R6/2 and WT mice. RT-qPCR from cortex, hippocampus and striatum mRNA were realized using specific primers for CYP46A1 cDNA. All RT-qPCR data were normalized using HPRT mRNA as an internal standard. Data are expressed as mean±SEM (n=3) (*$P<0.05$, **$P<0.005$, ns: non significant).

Figure 2:
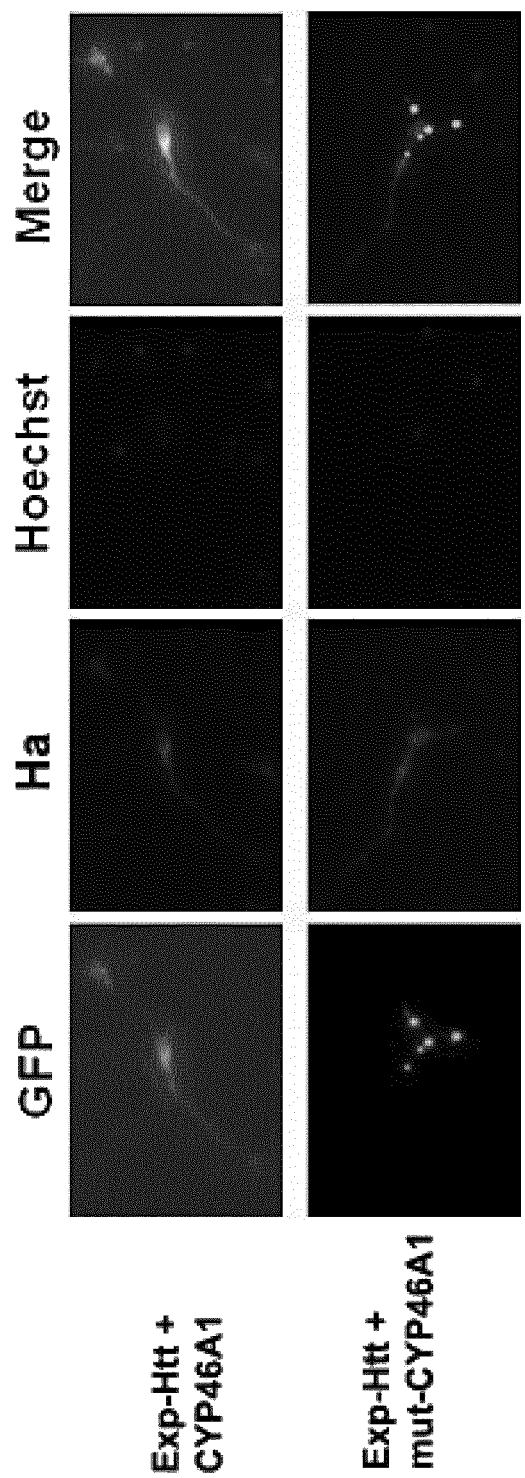

FIG. 2: Illustration of co-transfection assays. Exp-Htt expression was detected owing to GFP labeling (green), CYP46A1 or mut-CYP46A1 expression was detected owing to Ha immunolabeling (red). The viability of striatal neurons was evaluated on the basis of Hoechst staining (blue). Note the diffuse expression of Exp-Htt in the presence of CYP46A1, while an aggregate of Exp-Htt were formed in mut-CYP46A1 co-expressing neurons.

Figure 3:
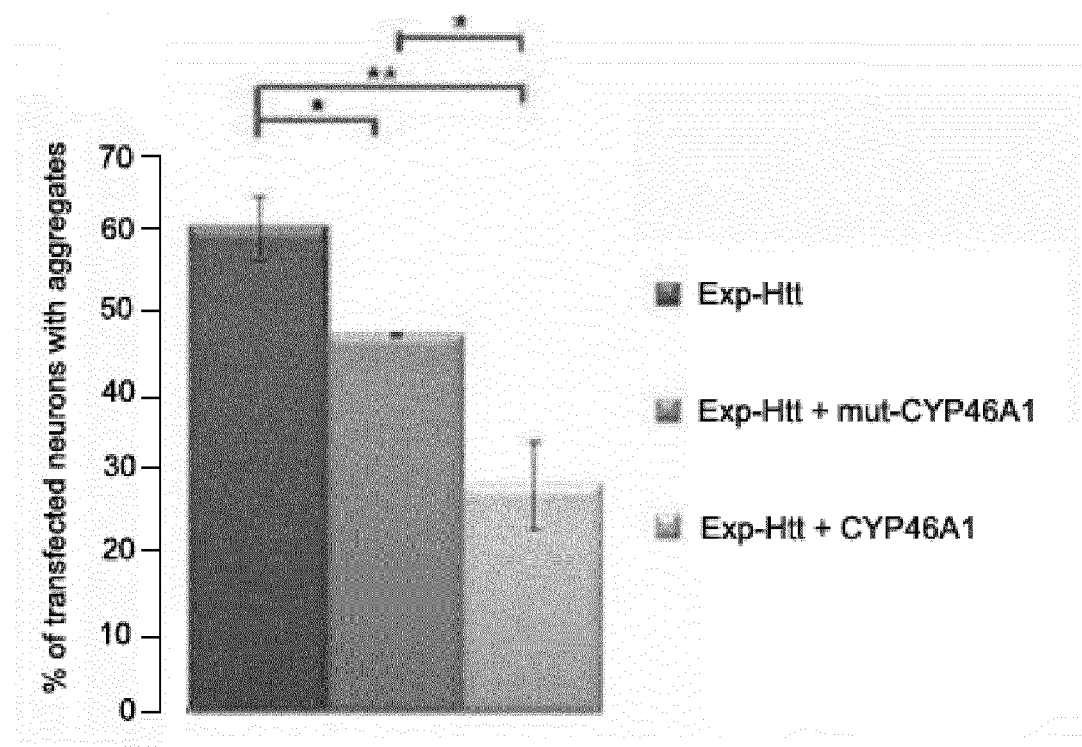

FIG. 3: Effect of CYP46A1 overexpression on ExpHtt-mediated aggregates formation. Primary striatal neurons were transfected with Exp-Htt or co-transfected with ExpHtt and mut-CYP46A1 or CYP46A1. Transfected neurons with aggregates of ExpHtt were quantified. Data were analyzed from at least 3 independent experiments (100 transfected neurons per condition and per experiment) and expressed as mean±SEM (*$P<0.05$, **$P<0.01$).

Figure 4:
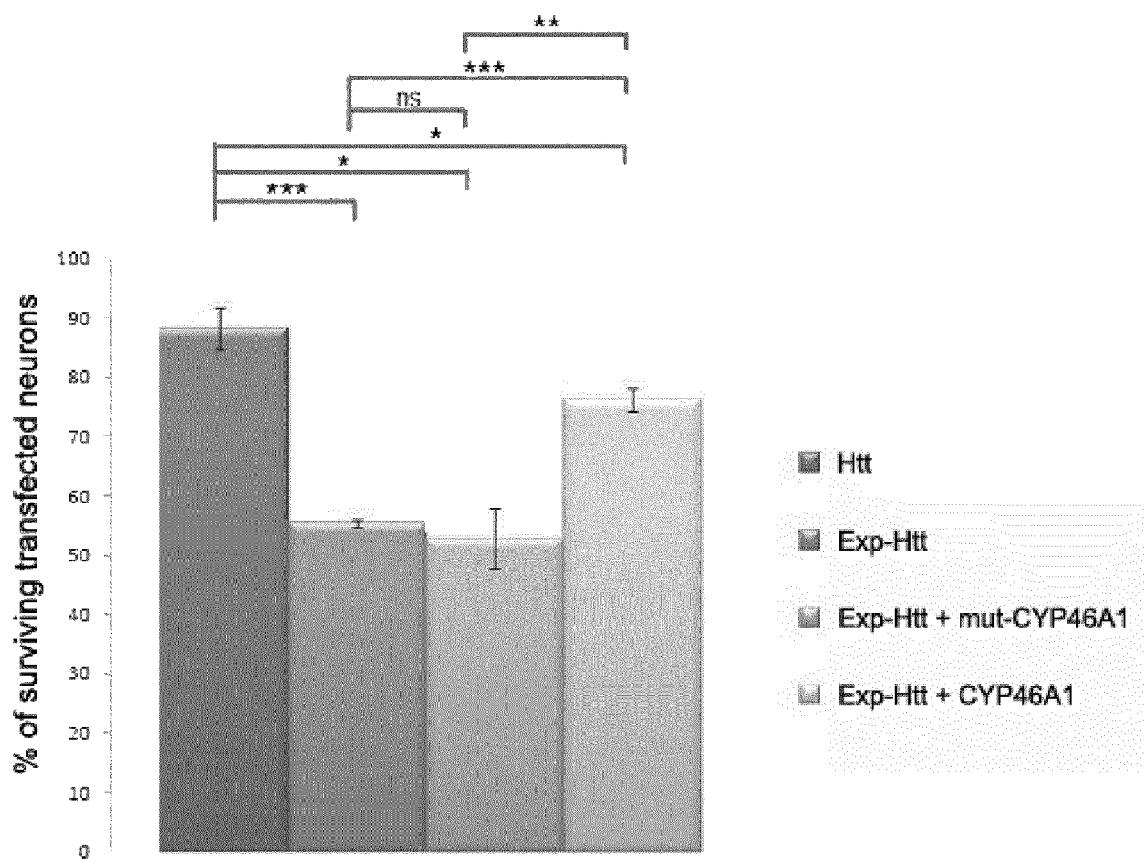

FIG. 4: Effect of CYP46A1 expression on ExpHtt-mediated striatal neurons death. Primary striatal neurons were transfected with Htt, Exp-Htt or co-transfected with Exp-Htt and mut-CYP46A1 (Exp-Htt+mut-CYP46A1) or CYP46A1 (Exp-Htt+CYP46A1). The percentage of surviving transfected neurons was quantified based on Hoechst labeling. Data were analyzed from at least 3 independent experiments (100 transfected neurons per condition and per experiment) and expressed as mean±SEM., *$P<0.05$, $P<0.005$, *$P<0.001$, ns: non significant).

Figure 5:
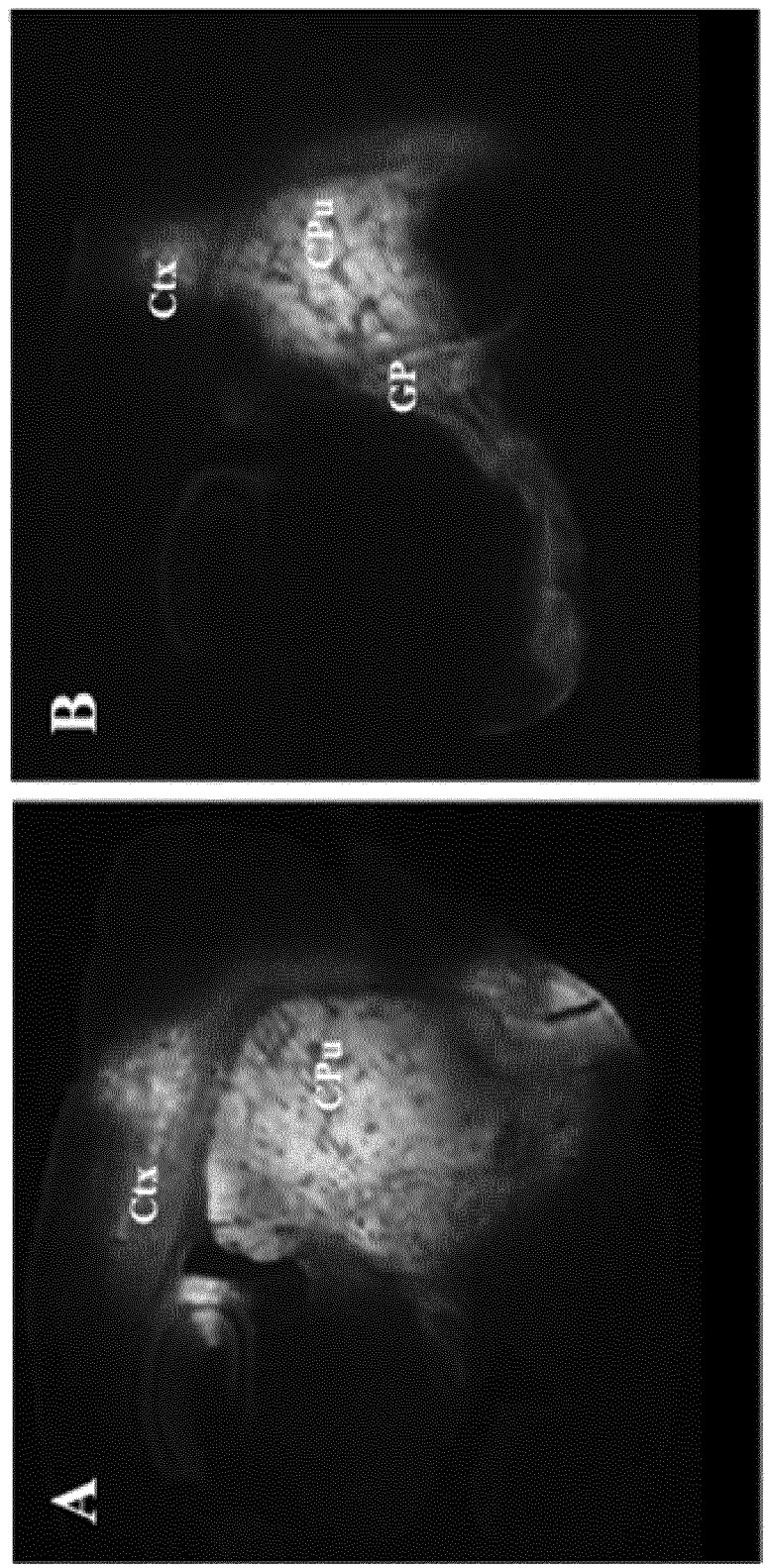

FIG. 5: Transduction of AAVrh.10 vector after stereotaxic injections into the striatum of WT mice. Sagittal sections (30 µm) of the brain were performed in mice 3 weeks after AAVrh.10-GFP delivery within the striatum. (A) Mouse brain sagittal sections, Lateral 2.28 mm. (B) Mouse brain sagittal section, Lateral 1.92 mm. Note that GFP staining (gray) showed a spread transduction of AAVrh.10 within the Caudate-Putamen (CPu) as well as two synaptically connected brain structures: Cortex (Ctx) and Globus Pallidus (GP).

Figure 6:
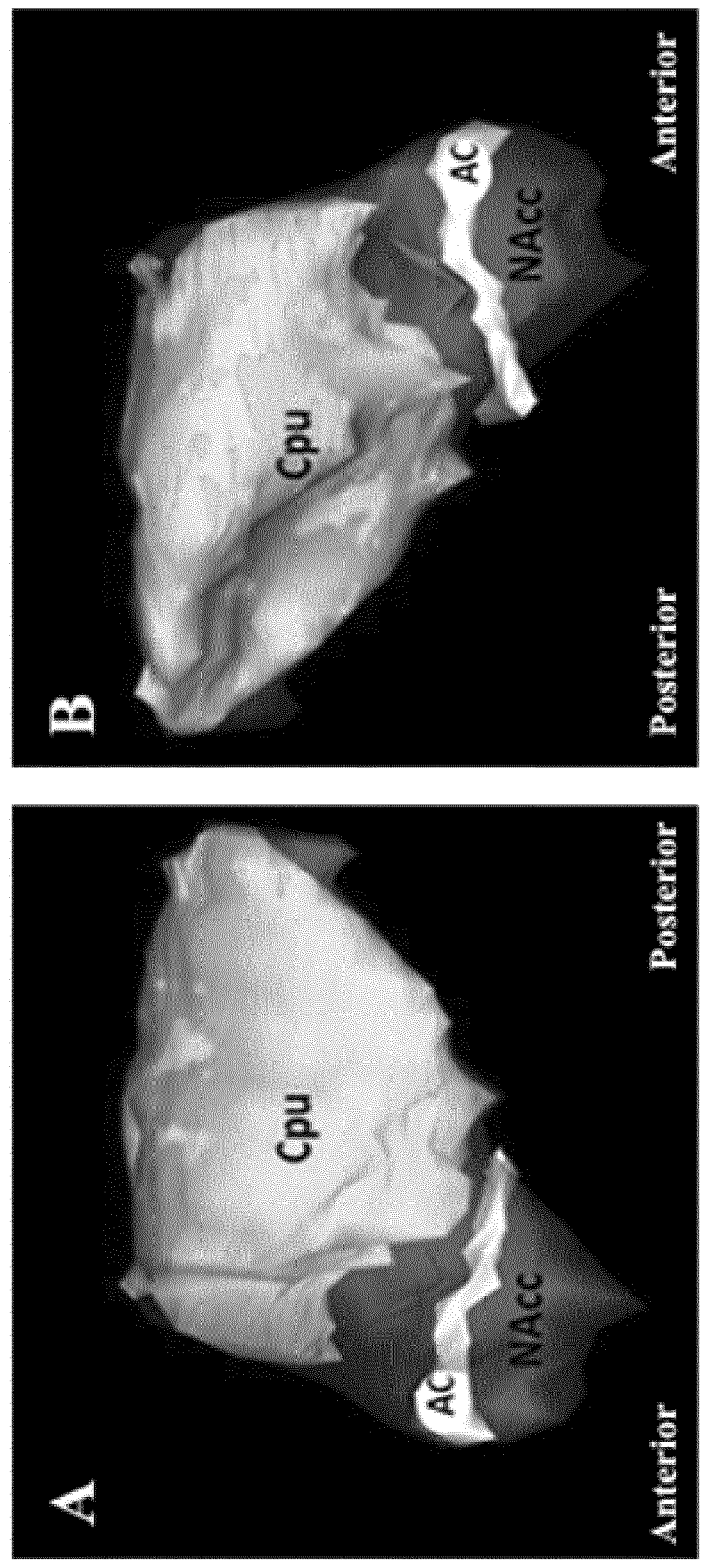

FIG. 6: Three-dimensional representation of the striatum transduced by AAVrh.10-GFP. Three weeks after AAVrh.10-GFP delivery within the striatum in WT mice, coronal sections (30 µm) of brain were performed followed by a tomographic reconstruction of green fluorescence emitted from striatum. (A) Sagittal view and (B) Medial view of the transduced-striatum (gray labeling). (CPu: Caudate-Putamen, AC: Anterior Commissure, NAcc: Nucleus Accumbens). Note that the whole dorsal striatum is transduced by AAvrh.10 (gray labeling).

Figure 7:
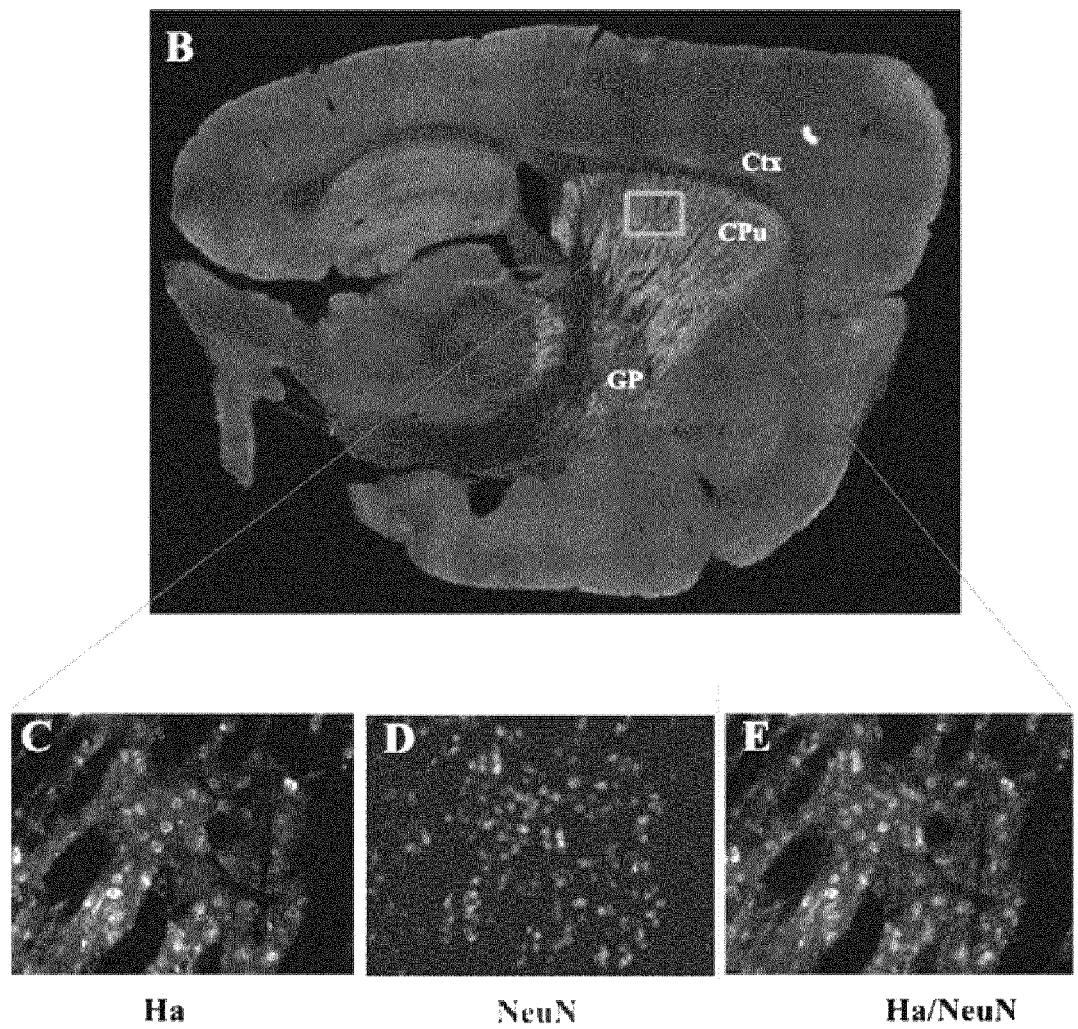

FIG. 7: Transduction and tropism of AAVrh.10-CYP46A1-Ha following stereotaxic injections into the striatum of WT mice. Sagittal sections (30 µm) of brain were studied by immunofluorescence 3 weeks after AAVrh.10-CYP46A1-Ha delivery within the striatum. (A) Representation of recombinant DNA of AAVrh.10-CYP46A1-Ha. Lateral 2.04 mm (B) CYP46A1-Ha expression was assessed by Ha immunohistological staining (light gray). (C-E) Higher magnification of Ha staining (C, white cytoplasmic labeling) combined with neuron specific marker staining (D, NeuN, white nuclear labeling). E) Fused image: Note the efficiency of AAVrh.10-CYP46A1-Ha transduction in the striatum and the neuronal tropism of AAVrh.10. CPu: Caudate-Putamen, GP: Globus Pallidus.

Figure 8:
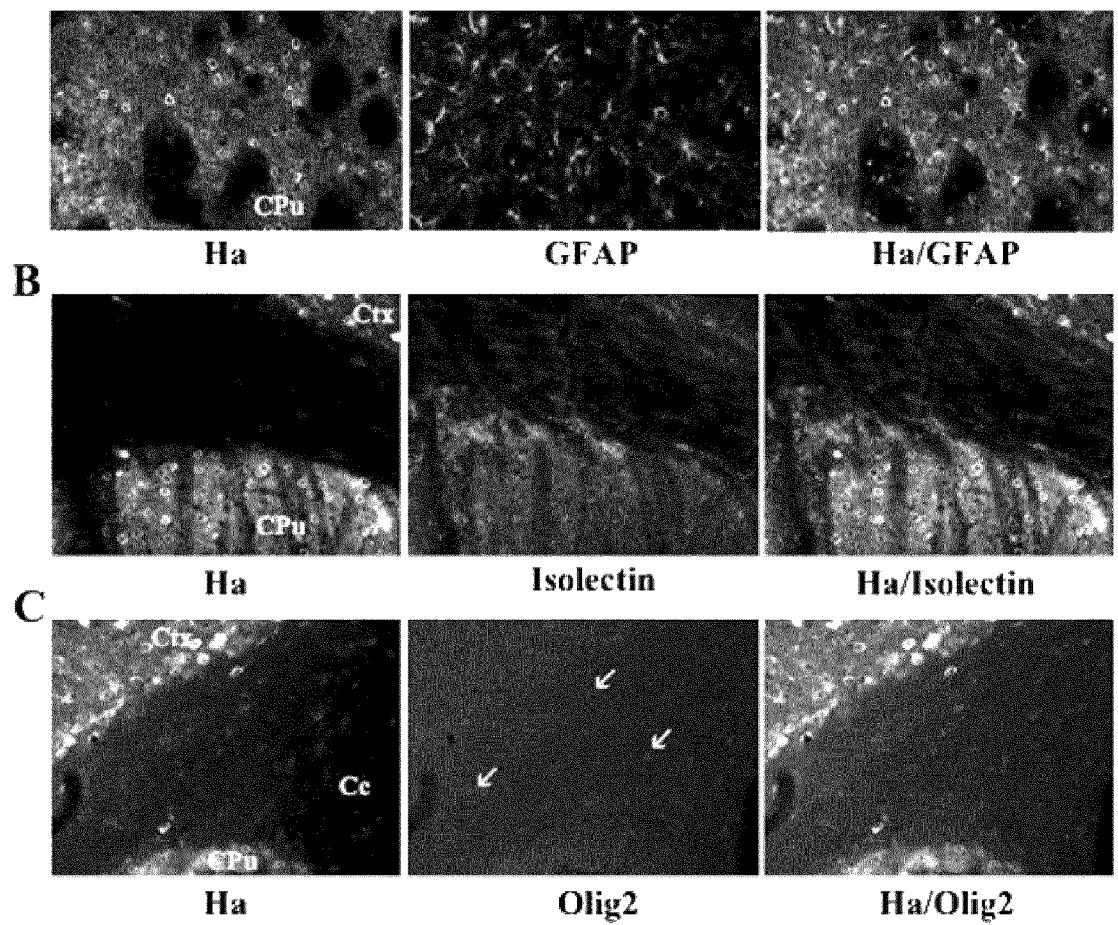

FIG. 8: Absence of CYP46A1-Ha expression in glial cells after stereotaxic injections of AAVrh10.CYP46A1-Ha into the striatum of WT mice. Coronal sections (30 µm) of brain were studied by immunofluorescence 3 weeks following AAVrh.10-CYP46A1-Ha delivery within the striatum. (A) Ha immunological staining (white cytoplasmic labeling) associated with a specific astrocytes staining using GFAP immunolabeling (white labeling). (B) Ha immunological staining (white cytoplasmic labeling) associated with a specific microglial cells labeling (white) and (C) Ha immunological staining (white) associated with a specific oligodendrocytes immunological staining (Olig2, redwhite, see arrows). Note the absence of CYP46A1-Ha expression in the glial cells. CPu: Caudate-Putamen, Cc: Corpus Callosum, Ctx: Cortex.

Figure 9:
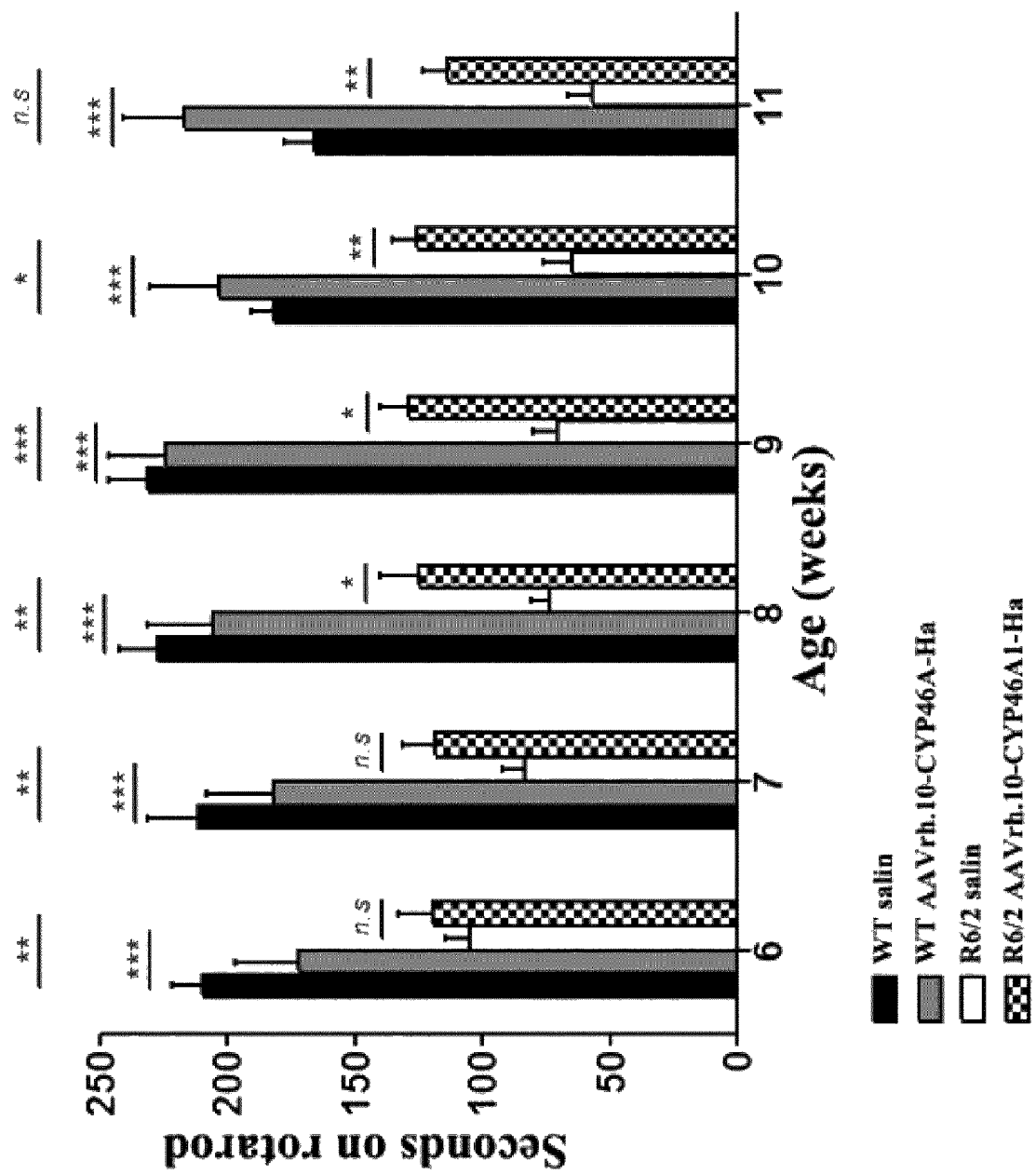

FIG. 9: Rotarod performance of WT and R6/2 mice injected with saline or AAVrh.10-CYP46A1-Ha. Motor performance on the rotarod were performed 2 weeks after AAVrh.10-CYP46A1-Ha delivery within the striatum in mice from 6 weeks of age through 11 weeks. Data are expressed as mean+/−SEM (*$P<0.05$, $P<0.001$, *$P<0.0001$) Statistical analysis revealed significant effect of AAVrh.10-CYP46A1-Ha on R6/2 mice rotarod performance from 8 weeks of age. WT saline (n=6) WT AAVrh.10-CYP46A1-Ha (n=8), R6/2 saline (n=13), R6/2 AAVrh.10 (n=12).

Figure 10:
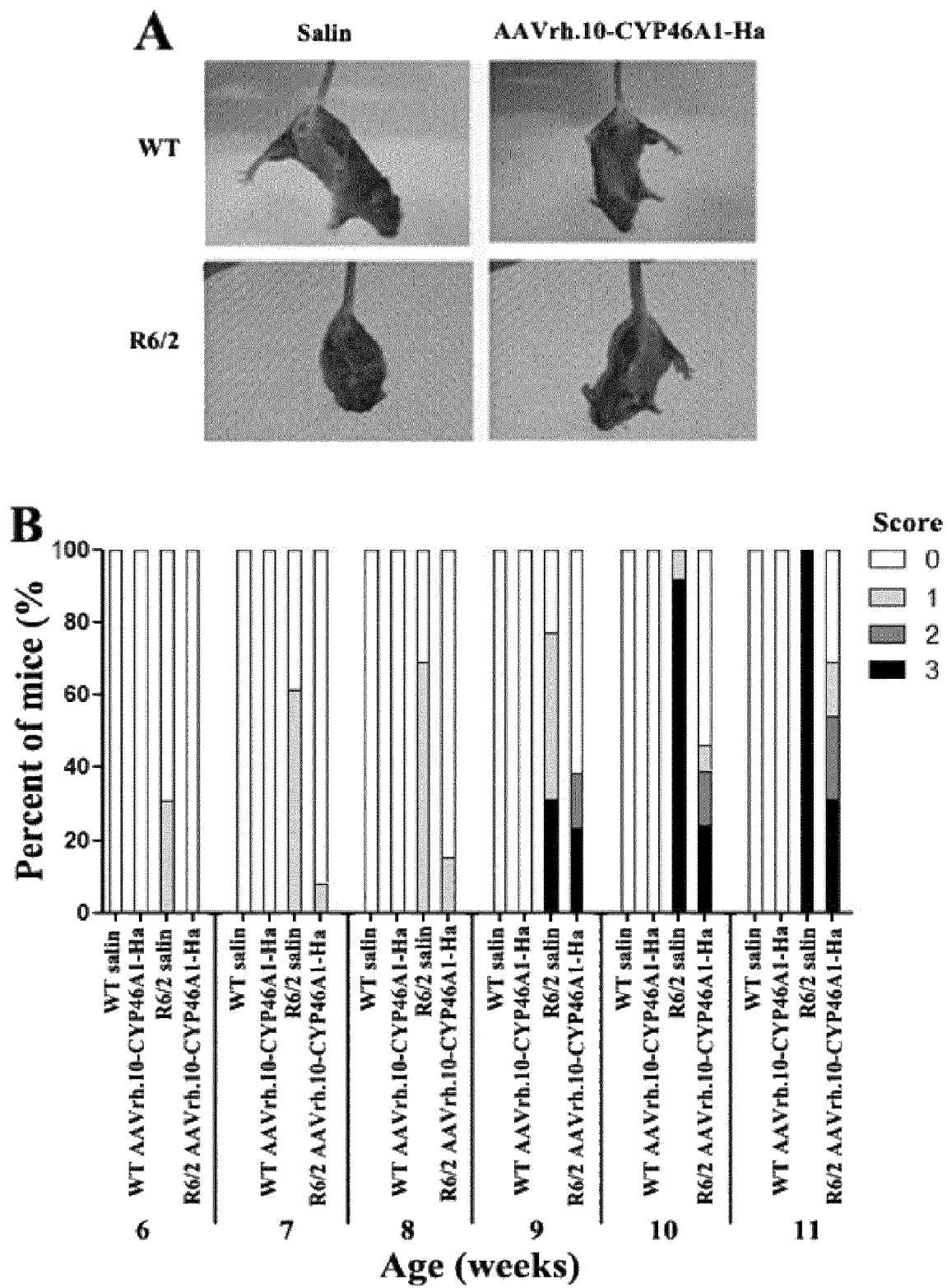

FIG. 10: Clasping scores of WT and R6/2 mice after stereotaxic injections of AAVrh10.CYP46A1-Ha or saline into the striatum. Clasping were performed 2 weeks after AAVrh.10-CYP46A1-Ha delivery within the striatum in mice from 6 weeks of age through 11 weeks. (A) Representative pictures of WT and R6/2 mice at 11 weeks old suspended by the tail. WT mice injected with saline or AAVrh.10-CYP46A1-ha showed helicoptering of limbs whereas R6/2 mice injected with saline showed both fore- and hindlimb clasping. AAVRh.10-CYP46A1-Ha injection in R6/2 mice has beneficial effects on fore- and hindlimb postures. (B) Quantification of clasping tests with four scores related to the severity of the phenotype. WT saline (n=6) WT AAVrh.10-CYP46A1-Ha (n=8), R6/2 saline (n=13), R6/2 AAVrh.10 (n=12).

EXAMPLES

Example 1

Effect of CYP46A1 In Vitro

Material & Methods
Mouse Husbandry:
Transgenic R6/2 mice and WT littermate were housed in a temperature-controlled room maintained on a light/dark cycle. Food and water were available ad libitum. R6/2 mice [B6CBA-TgN (HDexon1) 62], which express exon1 of the human mutant HD gene containing 115-150 CAGs under the control of the human IT15 gene promoter, were obtained from the Jackson Laboratory (Bar Harbor, Me., USA), by crossing ovarian transplant hemizygous females with males of their background strain B6CBAF1/J. Genotyping of transgenic mice was performed on tail DNA by PCR. The mice were housed in groups with a 12 h light/dark cycle and food and water ad libitum. Experiments were performed in accordance with standard ethical guidelines (U.S. National Institutes of Health publication n° 85-23, revised 1985, and the European Committee Guidelines on the Care and Use of Laboratory Animals directive 86/609/EEC).

RNA Extraction from Tissues and Quantitative Reverse Transcription-PCR Amplification:

Striatum, cortex and hippocampus were dissected from 6 weeks-old WT and R6/2 mice. Total mRNAs were isolated using RNeasy mini kit (Qiagen) using the manufacturer's instructions. Reverse transcription was performed using SuperScript III (Invitrogen) Four hundred nanograms of total mRNAs extracted from crude striatum, cortex and hippocampus were used as template for reverse transcription with the reverse transcription (RT) kit (SuperScript III-Invitrogen).

The resulting cDNA were used as a template for quantitative PCR (QPCR) performed in the Icycler detection system (Bio-Rad) using the ABsolute SYBR Green QPCR kit (AB-gene). Specific primers (Eurogentec S.A.) were designed for CYP46A1 cDNA amplification:

```
Forward:
                                      (SEQ ID NO: 3)
5'-TCCTCTCCTGTTCAGCACCT-3'

Reverse:
                                      (SEQ ID NO: 4)
5'-GGCCATGACAACTTTCACCT-3'
```

Absolute mRNA quantities were normalized with HPRT mRNA (hypoxanthine-guanine phosphoribosyltransferase), used as housekeeping gene. The following primers to amplify HPRT cDNA were as followed:

```
Forward:
                                      (SEQ ID NO 5)
5'-TTGCTCGAGATGTCATGAAGGA-3'

Reverse:
                                      (SEQ ID NO 6)
5'-AGCAGGTCAGCAAAGAACTTATAG-3'
```

Results represented are the mean of 3 different normalizations of CYP46A1 mRNA expression in R6/2 or WT mice.

Primary Striatal Culture:

Primary striatal neurons were dissected out from 14 days old embryos from pregnant Swiss mice (Janvier, Le Genest Saint Isle, France). Cell dissociation was performed with 1 mL of Trypsin-EDTA for 15 min and stopped by adding 1 mL of Complete Neurobasal (NBC) (Neurobasal supplemented with B27, antibiotic and Glutamine) to 300 µL of Fetal Calf Serum and 30 µL DNase I. After mechanic dissociation and incubation on ice for 5 minutes, the supernatant was taken and the pellet was resuspended in 1 mL NBC. The solution of striatal cells was centrifuged 5 min, 4° C., 900 rpm and the pellet was suspended in NBC.

Cell counting were plated on a poly-L-lysine-coated 4-wells (160000 cells per well) at 37° C., 5% CO2 in incubator.

Transfection:

After 7 days in culture, neurons grown in 4 well plates, were transiently transfected using lipofectamine (Invitrogen) with pcDNA constructs encoding the first exon of human Htt containing either 25 (Htt) or 103 (ExpHtt) continuous CAA or CAG repeats in frame with GFP (provided by HDF Resource Bank, UCLA). When indicated, striatal neurons were cotransfected with pcDNA constructs encoding the Wild Type CYP46A1 protein in frame with an Hemagglutinin tag (CYP46A1-Ha) or a Ha-tagged mutated version corresponding to a missense mutation (A1309C) devoid of enzymatic activity (CYP46A1-mut) (gift from Pr Aubourg). Three hours and half after transfection the medium was removed and replaced by NBC.

Immunohistochemistry, Aggregates Formation and Neuronal Death Analysis:

Striatal neurons were fixed in 2% paraformaldehyde in PBS for 40 minutes at room temperature and permeabilized with 0.3% triton in phosphate buffer saline (PBS) for 15 min and washed with PBS 1×0.1% triton for 5 min at room temperature. After washing with PBS, cells were preincubated with blocking buffer (PBS, 0.1% triton 5% NGS) for 20 min and washed with PBS 0.1% triton, 1% NGS for 5 min at room temperature. Primary antibody (Monoclonal mouse anti-Ha Covance, dilution 1/1000) was incubated in PBS 0.1% triton 1% NGS overnight at 4° C. After three washes with PBS 0.1% triton for 5 min, cells were incubated with the second antibody (Alexa 568 anti-mouse, dilution 1/1000 in PBS 0.1% triton 1% NGS). Three washes with PBS 0.1% triton were performed before nucleus labeling using Hoechst staining (1/20000 in PBS) for 5 min followed by 3 washing with PBS for 5 min. The cells were mounted under cover slips using a Vectashield medium (Vector Laboratories) and analyzed with a Leica DM4000B fluorescence microscope (×40). Aggregate formation was evaluated owing to GFP staining of Exp-Htt and quantified 24 h after transfection. Neuronal death was evaluated 48 h after transfection after Hoechst staining and neurons containing condensed or fragmented nuclei were scored as dying cells. Results presented are the results of three independent experiments and more than 100 transfected neurons were analyzed in each experiment.

Statistical Analysis:

All data were statistically analyzed using a student's t test and for all statistical analysis the difference between comparisons was considered to be significant when $P<0.05$.

Results

A. CYP46A1 mRNA Quantification in a Mouse Model of Huntington's Disease:

Dysfunction of the cholesterol biosynthesis has been described in HD (for review Valenza et al 2006). Since Exp-Htt is known to induce transcriptional dysregulation—specifically genes involved in neuronal survival and metabolism, wee reasoned that a deficiency of CYP46A1 mRNA expression could account, at least in part, for cholesterol deregulation and hence neuronal dysfunctions in HD. R6/2 mice are the more commonly used and the best characterized mice model of HD. These transgenic mice display an array of behavioral and regulatory changes that develop gradually until death, which occurs between 13 to 16 weeks-old. We measured CYP46A1 mRNA expression in cerebral tissues from 6 weeks-old R6/2 mice, along with their wild type littermate, using quantitative Reverse Transcriptase PCR. For each mice strain, RNAs were extracted from the cerebral cortex, hippocampus and striatum. CYP46A1 mRNA expression was slightly, but significantly down-regulated in the cerebral cortex of R6/2 mice when compared to wild type mice (FIG. 1). No significant alteration was found in the hippocampus. In the striatum of R6/2 mice, we found a strong decrease of CYP46A1 mRNA expression, when compared to the striatum of wild type mice (−50%; FIG. 1).

B. Influence of CYP46A1 Overexpression on Toxic Effects of ExpHtt in Primary Striatal Neurons:

The decrease of CYP46A1 mRNA expression observed in the striatum of R6/2 mice suggested a possible causal role in the pathogenesis of HD. To address this, we used a simple model system of striatal neuron dysfunctions induced by Exp-Htt, which was set up in the laboratory (Garcia et al., 2004; Charvin et al., 2005, Deyts et al., 2009). This model system consists in primary cultures of striatal neurons transiently transfected with a cDNA construct encoding the first exon of Htt with 25 polyglutamine (Htt) or 103 polyglutamine (Exp-Htt) stretch. In this cellular model, overexpression of Exp-Htt leads to spontaneous aggregates formation and death. These two parameters can be evaluated 24 and 48 hours after transfection, respectively. To analyze a possible protective role of CYP46A1, cDNA encoding the full length protein in its wild type (CYP46A1) or mutated form (mut-CYP46A1) were co-transfected along with Exp-Htt. Htt or Exp-Htt expression was detected owing to GFP labeling, whereas CYP46A1 and mut-CYP46A1 were detected after Ha-immunolabeling. In the co-transfection assays, all transfected neurons showed co-expression of GFP and Ha (FIG. 2).

B-1) Effect of CYP46A1 Overexpression on ExpHtt-Mediated Aggregates Formation:

Twenty-four hours after transfection of striatal neurons with the GFP-ExpHtt encoding plasmid, 58% of transfected neurons showed aggregates of Exp-Htt (FIG. 3). No aggregates were observed in GFP-Htt expressing neurons (data not shown). Co-expression of CYP46A1 with ExpHtt promoted a strong and significant decrease of aggregates formation (58% versus 27.5%) (FIG. 3). A slight but significant decrease of aggregates (58% versus 47%) was found with the inactive CYP46A1 mutant. In conclusion, overexpression of CYP46A1 protects striatal neurons from Exp-Htt aggregates formation.

B.2). Effect of CYP46A1 Expression on ExpHtt-Mediated Striatal Neurons Death:

Expression of ExpHtt in striatal neurons induced a significant decrease of survival when compared to Htt-expressing neurons (FIG. 4). Indeed, 48 h after transfection, 89% of Htt-expressing neurons were still alive after transfection whereas only 55% of Exp-Htt expressing neurons survive. Co-expression of mut-CYP46A1 with Exp-Htt did not protect against striatal death. By contrast, a neuroprotection was found in striatal neurons that co-expressed Exp-Htt and CYP46A1 (FIG. 4). Thus, the percentage of surviving neurons rouse to 76% in Exp-Htt+CYP46A1 transfected neurons, when compared to 55% in Exp-Htt only or 89% in Htt expressing neurons. Thus, CYP46A1 has a strong protective effect on neuronal death induced by ExpHtt.

Example 2

Effect of CYP46A1 In Vivo

Material and Methods

Striatal Delivery of AAVrh.10-GFP and AAVrh.10-CYP46A1-Ha in Mice

The two AAVrh10 vectors used contain an expression cassette consisting of the gfp cDNA (AAVrh.10-GFP) or human CYP46A1 cDNA in frame with a Hemagglutinin tag (AAVrh.10-CYP46A1-Ha) driven by a CMV/β-actin hybrid promoter surrounded by inverted terminal repeats of AAV2. Both AAVrh10 vectors were produced in Pr Ronald G. Crystal laboratory (Department of Genetic Medicine, Weill Medical College of Cornell University, New York, N.Y., USA). At 4 weeks of age WT or R6/2 mice were anesthetized by intraperitoneal injection of Ketamine/xylasine solution (Ketamine 100 mg/kg, Merial, Lyon, France and xylasine 10 mg/kg, Bayer Health Care, Germany) and placed in a stereotaxic apparatus (Kopf) in a conventional PC2 (physical containment level 2) laboratory. Mice received AAVrh.10 GFP (10³ vg/ml) or AAVrh.10 CYP46A1-Ha (1.6 10¹² vg/ml) or saline solution (NaCl 0.001%) administration bilaterally in striatum (A/P+0.5 mm, M/L+/−2.1 mm, D/V −3.35 mm), the injected volume was 2 µl at a rate of 0.2 µl/min. After surgery, mice recovered 72 hours in a PC2 animal facility and transferred to a phenotype platform with a PC1 animal facility.

Evaluation of AAVrh.10 Transduction and Tropism in Brain after In Vivo Delivery

Three weeks after AAVrh.10-GFP or AAVrh.10-CYP46A1-Ha delivery in WT mouse striatum, the animals were anesthetized by sodium pentobarbital overdose 250 mg/kg (Sanofi, Paris, France), perfused transcardially with a 4% Paraformaldehyde solution delivered with a peristaltic pump at 25 ml/min for 5 min. Brains were then postfixed overnight in the same solution and stored at 4° C. Coronal or Sagittal Sections (30 µm) were cut with a vibratome (Leica Microsystems, Rueil-Malmaison, France) and kept in a solution containing 30% ethylene glycol, 30% glycerol, and 0.1 M phosphate buffer at −20° C. until processing for histology analysis.

AAVrh.10 Transduction

Brain AAVrh.10 transduction was determined 3 weeks after AAVrh.10-GFP vector delivery in WT mice. After three rinses in TBS, brain sections were mounted under cover slips with Vectashield (Vector Laboratories) and GFP staining was analyzed on coronal brain sections over the rostro-caudal extension of the brain using epifluorescence motorized microscope (Zeiss) equipped with a CCD camera connected to a PC computer. Tomographic reconstruction of green fluorescence emitted from striatum was performed from mosaic pictures (Mastronarde, D. N., 1997) followed by a three-dimensional representation thanks to IMOD software (Kremer et al, 1996).

AAVrh.10 Tropism

Brain AAVrh.10 tropism was studied 3 weeks after AAVrh.10 CYP46A1Ha vector delivery in striatum WT mice. Specific neuronal and glial markers were assessed by immunohistochemistry. Free-floating sections were rinsed in TBS and incubated for 15 min with 0.2% Triton X-100 in TBS. After three rinses, the floating sections were saturated for 1 h at room temperature with 10% NGS in TBS. The sections were then rinsed three times in TBS and incubated with the primary antibody (Ha 1/500, Covance; NeuN 1/200, AbCys Vector; Olig2 1/1000, Millipore; GFAP 1/1000, Dako; Isolectine 1/1000, Chemicon) overnight at 4° C. in TBS1X-NGS 5%. The sections were then incubated for 90 min at room temperature with the Alexa Fluor secondary antibody (1/1000, Invitrogen, Carlsbad, Calif., USA). After three rinses in TBS, tissue sections were mounted under cover slips with Vectashield (Vector Laboratories) for fluorescence microscopy.

In Vivo Study of AAVrh10-CYP46A1Ha in HD Mouse Model

The clasping test and the rotarod performance were tested two weeks after AAVrh.10-CYP46A1-Ha delivery or saline injection in WT and R6/2 mice. For clasping score, mice were tested once every week from 6 weeks to 11 weeks of age. Mice were suspended by the tail for 30 seconds and the clasping phenotype was graded to a particular level according to the following scale: 0, no clasping; 1, clasping of the forelimb only; 2, clasping of both fore and hind limbs once or twice; 3, clasping of both fore- and hind limbs more than 3 times or more than 5 seconds. For rotarod performance, mice were tested over 3 consecutive days every single week from 6 weeks to 11 weeks of age. A training trial was performed at 5 weeks of age but the data were not included in the final results. Daily sessions included a 5 minutes training trial at 4 RPM. At least 1 hour later, mice were tested in three 5 minutes trials with an accelerating speed (from 0 to 40 RPM in 5 minutes) separated by a 30 minutes inter-trial interval. The latency to fall from the rotarod was recorded. Mice remaining on the rotarod for more than 5 minutes were removed and their time scored as 300 seconds.

Statistical Analysis

Two way ANOVA analysis followed by Bonferroni test was used for rotarod performance comparisons (*, $P<0.05$; , $P<0.01$; *, $P<0.001$). For all statistical analysis the difference between comparisons was considered to be significant when $P<0.05$.

Results

C. CYP46A1 Delivery In Vivo Using the AAVrh.10 Vector

C1. Efficacy of Transduction

In order to express CYP46A1 in the striatum of mice, we decided to use the AAVrh.10 vector. In a first step, we used AAVrh.10 expressing the cDNA encoding GFP. The AAVrh.10-GFP vector was administered in the striatum, in vivo, using micro-injections (see the method section). Expression of GFP was analyzed from sagittal and coronal section 3 weeks after injection. Using our parameters, GFP was observable within the whole extension of the dorsal striatum, along with the globus pallidus and cerebral cortex, two brain structures synaptically connected to the striatum (FIGS. 5A and 5B). A three-dimensional representation of coronal sections expressing GFP was performed, showing GFP expression in 63% of the striatum, ie the whole dorsal striatum (FIGS. 6A and 6B).

C2. Neuronal Tropism

Then, we used the AAVrh.10-CYP46A1-Ha vector (FIG. 7A) according to the same experimental conditions (2 microliters at 1.6 1012 vg/ml)). CYP46A1 expression induced by this vector was revealed using the Ha immunocytodetection that was found, as expected, within the whole dorsal striatum (Caudate Putamen-CpU) (FIG. 7B). At the cellular level, we found a cytoplasmic localization of the CYP46A1-Ha product (FIG. 7C). As assessed by double immunocytochemical detection, the AAVrh10 vector had a strong neuronal tropism, since Ha labeling perfectly overlapped with the Neuronal marker NeuN (FIG. 7C-D)). Further experiments were performed using glial markers, for astrocytes (GFAP), astroglia (Isolectine) and oligodendrocytes (Olig2). None of these markers co-labeled with Ha (FIG. 8A-C). Thus, altogether these data indicate that the AAVrh10-CYP46A1-Ha vector has a strict neuronal tropism.

D. AAVrh.10-Cyp46A1-Ha Delivery in R6/2 Mouse Model of HD

D1. Behavioral Protection The transgenic mouse model of HD, the R6/2 mice that overexpress the first exon of human HTT gene with 150CAG repeats, and their wild type littermate, were used in this part of the study. Both strains were bilaterally injected within the striatum with the AAVrh.10-CYP46A1-Ha vector (n=6 for wild type mice and n=12-13 for R6/2 mice) at 4 weeks post-natal. Control groups were injected with a saline solution according to the same experimental conditions.

Behavioral performances of the injected mice were evaluated from 6 weeks to 11 weeks post-natal using the Rotarod (FIG. 9) and the clasping (FIG. 10) tests. Whatever the striatal injection (ie saline or AAVrh.10-CYP46A1-Ha), the wild type mice showed the same behavioral performance in the Rotarod test (FIG. 9), with a slight decline between 9 and 11 weeks post-natal, which probably reflected a slight decrease in motivation in performing this test. The R6/2 mice injected with saline and AAVrh.10-CYP46A1-Ha showed significant lower performance than wild type mice from 6 to 11 weeks. (FIG. 9). Nevertheless, while saline-injected R6/2 mice had a progressive decline in this test between 6 and 11 weeks, AAVrh10-CYP46A1-Ha-injected R6/2 mice remained at the same level of performance (FIG. 9). At 11 weeks post-natal (7 weeks post-injection), AAVrh.10-CYP46A1-Ha-injected R/6 mice were not significantly different from saline-injected wild type mice.

R6/2 mice injected with saline showed a progressive alteration in the hind limbs clasping response during tail suspension (FIG. 10A). At 11 weeks post-natal almost 100% of these mice reached the maximal score (clasping of both fore- and hind limbs more than 5 seconds). The R6/2 mice injected with AAVrh10-CYP46A-Ha showed a delay in their response and significant lower score at 11 weeks, ie only 30% of these mice showed a score 3 (FIG. 10B). Altogether these data indicate that AAVrh.10-CYP46A1-Ha alleviates locomotor deterioration induced by the mutation in HD.

REFERENCES

Throughout this application, various references describe the state of the art to which this invention pertains. The disclosures of these references are hereby incorporated by reference into the present disclosure.

Cearley C N, Wolfe J H. Mol Ther. 2006 March; 13(3):528-37 et Cearley C N, Vandenberghe L H, Parente M K, Carnish E R, Wilson J M, Wolfe J H. Mol Ther. 2008 October; 16(10):1710-8

Charvin, D., Vanhoutte, P., Pages, C., Borrelli, E., and Caboche, J. (2005) Unraveling a role for dopamine in Huntington's disease: the dual role of reactive oxygen species and D2 receptor stimulation. Proceedings of the National Academy of Sciences of the United States of America 102, 12218-12223. Deyts C, Galan-Rodriguez B, Martin E, Bouveyron N, Roze E, Charvin D, Caboche J, Bétuing S. (2009) Dopamine D2-receptor stimulation potentiates PolyQ-Huntingtin-induced mouse striatal neuron dysfunctions via Rho/ROCKII activation PLoS One. December 15; 4(12):e8287

Garcia M, Charvin D, Caboche J. (2004) Expanded-huntingtin activates the c-Jun terminal kinase/c-Jun pathway prior to aggregate formation in traital neurons in culture Neuroscience. 2004; 127(4):859-70.

Roze E, Betuing S, Deyts C, Marcon E, Brami-Cherrier K, Pagès C, Humbert S, Mérienne K, Caboche J. (2008) Mitogen- and stress-activated protein kinase-1 deficiency is involved in expanded-huntingtin-induced transcriptional dysregulation and striatal death. FASEB J. 22(4):1083-93.

Valenza M, Cattaneo E (2006) Cholesterol dysfunction in neurodegenerative diseases: is Huntington's disease in the list. Prog Neurobiol. 80(4):165-76.

The invention claimed is:

1. A method of treating Huntington's disease in a subject in need thereof, comprising
    administering to said subject a vector comprising a nucleic acid sequence that encodes cholesterol 24-hydroxylase.
2. The method of claim 1, wherein said nucleic acid sequence encodes the amino acid sequence set forth in SEQ ID NO: 2.
3. The method of claim 1, wherein said nucleic acid sequence comprises the nucleic acid sequence set forth in SEQ ID NO: 1.
4. The method of claim 1, wherein said vector is selected from the group consisting of an adenovirus vector, a retrovirus vector, a herpes virus vector and an Adeno-Associated Virus (AAV) vector.
5. The method of claim 4, wherein said vector is an AAV vector.
6. The method of claim 5, wherein said vector is an AAV vector selected from the group consisting of AAV1, AAV2, AAV3, AAV4, AA5, AAV6, AAV7, AAV8, AAV9, and AAV10.
7. The method of claim 6, wherein said AAV vector is an AAV10 vector.
8. The method of claim 1, wherein said vector is administered directly into the brain of the subject.
9. The method of claim 8, wherein said vector is administered by stereotaxic microinjection.
10. The method of claim 9, wherein said vector is administered to the ruber nucleus, corpus amygdaloideum, entorhinal cortex and neurons in ventralis lateralis, or to the anterior nuclei of the thalamus.
11. The method of claim 1, wherein said vector is administered by intravenous injection.
12. The method of claim 1, wherein said vector is administered by intrathecal injection.
13. The method of claim 1, wherein said vector is administered into the ventricles.

* * * * *

SEQUENCE LISTING

<160> NUMBER OF SEQ ID NOS: 6

<210> SEQ ID NO 1
<211> LENGTH: 2138
<212> TYPE: DNA
<213> ORGANISM: Homo sapiens

<400> SEQUENCE: 1

| | | | | | | |
|---|---|---|---|---|---|---|
| atgagcccg | ggctgctgct | gctcggcagc | gccgtcctgc | tcgccttcgg | cctctgctgc | 60 |
| accttcgtgc | accgcgctcg | cagccgctac | gagcacatcc | ccgggccgcc | gcggcccagt | 120 |
| ttccttctag | gacacctccc | ctgcttttgg | aaaaaggatg | aggttggtgg | ccgtgtgctc | 180 |
| caagatgtgt | ttttggattg | ggctaagaag | tatggacctg | ttgtgcgggt | caacgtcttc | 240 |
| cacaaaacct | cagtcatcgt | cacgagtcct | gagtcggtta | agaagttcct | gatgtcaacc | 300 |
| aagtacaaca | aggactccaa | gatgtaccgt | gcgctccaga | ctgtgtttgg | tgagagactc | 360 |
| ttcggccaag | gcttggtgtc | cgaatgcaac | tatgagcgct | ggcacaagca | gcggagagtc | 420 |
| atagacctgg | ccttcagccg | gagctccttg | gttagcttaa | tggaaacatt | caacgagaag | 480 |
| gctgagcagc | tggtggagat | tctagaagcc | aaggcagatg | gcagacccc | agtgtccatg | 540 |
| caggacatgc | tgacctacac | cgccatggac | atcctggcca | aggcagcttt | tgggatggag | 600 |
| accagtatgc | tgctgggtgc | ccagaagcct | ctgtcccagg | cagtgaaact | tatgttggag | 660 |
| ggaatcactg | cgtcccgcaa | cactctggca | agttcctgc | agggaagag | gaagcagctc | 720 |
| cgggaggtcc | gggagagcat | tcgcttcctg | cgccaggtgg | gcagggactg | ggtccagcgc | 780 |
| cgccgggaag | ccctgaagag | gggcgaggag | gttcctgccg | acatcctcac | acagattctg | 840 |
| aaagctgaag | agggagccca | ggacgacgag | ggtctgctgg | acaacttcgt | caccttcttc | 900 |
| attgctggtc | acgagaccct | tgccaaccac | ttggcgttca | cagtgatgga | gctgtctcgc | 960 |
| cagccagaga | tcgtggcaag | gctgcaggcc | gaggtggatg | aggtcattgg | ttctaagagg | 1020 |
| tacctggatt | tcgaggacct | ggggagactg | cagtacctgt | cccaggtcct | caaagagtcg | 1080 |
| ctgaggctgt | accccaccagc | atggggcacc | tttcgcctgc | tggaagagga | gaccttgatt | 1140 |
| gatgggtca | gagtccccgg | caacaccccg | ctcttgttca | gcacctatgt | catggggcgg | 1200 |
| atggacacat | actttgagga | cccgctgact | ttcaaccccg | atcgcttcgg | ccctggagca | 1260 |
| cccaagccac | ggttcaccta | cttccccttc | tccctgggcc | accgctcctg | catcgggcag | 1320 |
| cagtttgctc | agatggaggt | gaaggtggtc | atggcaaagc | tgctgcagag | gctggagttc | 1380 |
| cggctggtgc | ccgggcagcg | cttcgggctg | caggagcagg | ccacactcaa | gccactggac | 1440 |
| cccgtgctgt | gcaccctgcg | gccccgcggc | tggcagcccg | cacccccacc | accccctgc | 1500 |
| tgagggggcc | tccaggcagg | acgagactcc | tcgggcaagg | gccgtgcccg | cccacctctg | 1560 |
| ctgcccacgg | ccacccaccc | ttctccctg | ccccgtcccc | tgggccaccc | ttcacgctgg | 1620 |
| cttccagcgg | gccctctgcc | gaccgcctgc | ttcacacccc | tcagcgctcc | ctgtcgcctg | 1680 |
| cggactccat | ggcccttcct | ggactggccc | ttgcccaact | cccagccacc | accactgtcc | 1740 |
| ctaccactga | gcccttgcac | aggccacttg | ctcagacgag | acaccctaac | tcttgctcac | 1800 |
| tccctaaagc | cctcttcagg | ggtcacctcc | tccaagaagc | cctccttgcc | acccccgcc | 1860 |
| ggcaggggcc | cctcctctgt | gctccctcgg | tcacctgtgc | tacctctaac | accacactga | 1920 |
| ccacactgta | tcgtgagtgt | ccgttgacgt | gaccaattgc | cctgccaggc | tgtcagcgcc | 1980 |
| tcaagggtag | ggtctgcgtg | tgatttgtct | ctgagccccc | tgtgcccacc | cagggcccgg | 2040 |
| cacagagtcg | atgctcaata | aatgtgtgtt | gactgcaaaa | aaaaaaaaaa | aaaaaaaaa | 2100 | aaaaaaaaaa aaaaaaaaaa aaaaaaaaaa aaaaaaa         2138

<210> SEQ ID NO 2
<211> LENGTH: 500
<212> TYPE: PRT
<213> ORGANISM: Homo sapiens

<400> SEQUENCE: 2

```
Met Ser Pro Gly Leu Leu Leu Gly Ser Ala Val Leu Leu Ala Phe
1               5                   10                  15

Gly Leu Cys Cys Thr Phe Val His Arg Ala Arg Ser Arg Tyr Glu His
            20                  25                  30

Ile Pro Gly Pro Pro Arg Pro Ser Phe Leu Leu Gly His Leu Pro Cys
                35                  40                  45

Phe Trp Lys Lys Asp Glu Val Gly Gly Arg Val Leu Gln Asp Val Phe
50                  55                  60

Leu Asp Trp Ala Lys Lys Tyr Gly Pro Val Val Arg Val Asn Val Phe
65                  70                  75                  80

His Lys Thr Ser Val Ile Val Thr Ser Pro Glu Ser Val Lys Lys Phe
                85                  90                  95

Leu Met Ser Thr Lys Tyr Asn Lys Asp Ser Lys Met Tyr Arg Ala Leu
            100                 105                 110

Gln Thr Val Phe Gly Glu Arg Leu Phe Gly Gln Gly Leu Val Ser Glu
        115                 120                 125

Cys Asn Tyr Glu Arg Trp His Lys Gln Arg Arg Val Ile Asp Leu Ala
130                 135                 140

Phe Ser Arg Ser Ser Leu Val Ser Leu Met Glu Thr Phe Asn Glu Lys
145                 150                 155                 160

Ala Glu Gln Leu Val Glu Ile Leu Glu Ala Lys Ala Asp Gly Gln Thr
                165                 170                 175

Pro Val Ser Met Gln Asp Met Leu Thr Tyr Thr Ala Met Asp Ile Leu
            180                 185                 190

Ala Lys Ala Ala Phe Gly Met Glu Thr Ser Met Leu Leu Gly Ala Gln
        195                 200                 205

Lys Pro Leu Ser Gln Ala Val Lys Leu Met Leu Glu Gly Ile Thr Ala
210                 215                 220

Ser Arg Asn Thr Leu Ala Lys Phe Leu Pro Gly Lys Arg Lys Gln Leu
225                 230                 235                 240

Arg Glu Val Arg Glu Ser Ile Arg Phe Leu Arg Gln Val Gly Arg Asp
                245                 250                 255

Trp Val Gln Arg Arg Arg Glu Ala Leu Lys Arg Gly Glu Glu Val Pro
            260                 265                 270

Ala Asp Ile Leu Thr Gln Ile Leu Lys Ala Glu Glu Gly Ala Gln Asp
        275                 280                 285

Asp Glu Gly Leu Leu Asp Asn Phe Val Thr Phe Phe Ile Ala Gly His
290                 295                 300

Glu Thr Ser Ala Asn His Leu Ala Phe Thr Val Met Glu Leu Ser Arg
305                 310                 315                 320

Gln Pro Glu Ile Val Ala Arg Leu Gln Ala Glu Val Asp Glu Val Ile
                325                 330                 335

Gly Ser Lys Arg Tyr Leu Asp Phe Glu Asp Leu Gly Arg Leu Gln Tyr
            340                 345                 350

Leu Ser Gln Val Leu Lys Glu Ser Leu Arg Leu Tyr Pro Pro Ala Trp
        355                 360                 365
```

-continued

```
Gly Thr Phe Arg Leu Leu Glu Glu Thr Leu Ile Asp Gly Val Arg
        370                 375                 380

Val Pro Gly Asn Thr Pro Leu Leu Phe Ser Thr Tyr Val Met Gly Arg
385                 390                 395                 400

Met Asp Thr Tyr Phe Glu Asp Pro Leu Thr Phe Asn Pro Asp Arg Phe
                405                 410                 415

Gly Pro Gly Ala Pro Lys Pro Arg Phe Thr Tyr Phe Pro Phe Ser Leu
            420                 425                 430

Gly His Arg Ser Cys Ile Gly Gln Gln Phe Ala Gln Met Glu Val Lys
        435                 440                 445

Val Val Met Ala Lys Leu Leu Gln Arg Leu Glu Phe Arg Leu Val Pro
    450                 455                 460

Gly Gln Arg Phe Gly Leu Gln Glu Gln Ala Thr Leu Lys Pro Leu Asp
465                 470                 475                 480

Pro Val Leu Cys Thr Leu Arg Pro Arg Gly Trp Gln Pro Ala Pro Pro
                485                 490                 495

Pro Pro Pro Cys
            500

<210> SEQ ID NO 3
<211> LENGTH: 20
<212> TYPE: DNA
<213> ORGANISM: Artificial
<220> FEATURE:
<223> OTHER INFORMATION: Synthetic oligonucleotide Primer

<400> SEQUENCE: 3
tcctctcctg ttcagcacct                                                 20

<210> SEQ ID NO 4
<211> LENGTH: 20
<212> TYPE: DNA
<213> ORGANISM: Artificial
<220> FEATURE:
<223> OTHER INFORMATION: Synthetic oligonucleotide Primer

<400> SEQUENCE: 4
ggccatgaca actttcacct                                                 20

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide Primer

<400> SEQUENCE: 5
ttgctcgaga tgtcatgaag ga                                              22

<210> SEQ ID NO 6
<211> LENGTH: 24
<212> TYPE: DNA
<213> ORGANISM: Artificial
<220> FEATURE:
<223> OTHER INFORMATION: Synthetic oligonucleotide Primer

<400> SEQUENCE: 6
agcaggtcag caaagaactt atag                                            24
```